(12) United States Patent
Nakayama

(10) Patent No.: US 9,524,022 B2
(45) Date of Patent: Dec. 20, 2016

(54) MEDICAL EQUIPMENT

(71) Applicant: OLYMPUS CORPORATION, Tokyo (JP)

(72) Inventor: Shingo Nakayama, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 264 days.

(21) Appl. No.: 14/170,856

(22) Filed: Feb. 3, 2014

(65) Prior Publication Data

US 2014/0148821 A1 May 29, 2014

Related U.S. Application Data

(63) Continuation of application No. PCT/JP2012/070407, filed on Aug. 3, 2012.

(Continued)

(51) Int. Cl.
*A61B 19/00* (2006.01)
*G06F 3/01* (2006.01)
(Continued)

(52) U.S. Cl.
CPC .............. *G06F 3/01* (2013.01); *A61B 17/29* (2013.01); *A61B 17/32002* (2013.01); *A61B 18/1402* (2013.01); *A61B 34/30* (2016.02); *A61B 34/37* (2016.02); *A61B 46/10* (2016.02); *B25J 9/1689* (2013.01); *B25J 13/02* (2013.01); *A61B 17/068* (2013.01); *A61B 34/25* (2016.02); *A61B 46/23* (2016.02); *A61B 2017/00119* (2013.01); *A61B 2017/00477* (2013.01);
(Continued)

(58) Field of Classification Search
CPC ... A61B 17/128; A61B 17/1285; A61B 17/10; A61B 17/068; A61B 17/28; A61B 17/29; A61B 2017/0046; A61B 2017/00464
See application file for complete search history.

(56) References Cited

U.S. PATENT DOCUMENTS 3,139,990 A  7/1964 Jelatis et al.
3,923,166 A  12/1975 Fletcher et al.
(Continued)

FOREIGN PATENT DOCUMENTS

CN  101027010 A  8/2007
CN  101167658 A  4/2008
(Continued)

OTHER PUBLICATIONS

International Search Report dated Oct. 23, 2012 issued in PCT/JP2012/070414.
(Continued)

*Primary Examiner* — Melanie Tyson
(74) *Attorney, Agent, or Firm* — Scully, Scott, Murphy & Presser, P.C.

(57) ABSTRACT

A medical equipment includes a surgical instrument having a movable part to perform medical treatment on a target spot, an actuator configured to operate the movable part, and a detachable interface installed on the surgical instrument and configured to attachably and detachably couple the surgical instrument to the actuator. The detachable interface has an origin return mechanism configured to move the movable part to a predetermined origin position when the surgical instrument is detached from the actuator.

15 Claims, 10 Drawing Sheets

Related U.S. Application Data

(60) Provisional application No. 61/515,203, filed on Aug. 4, 2011.

(51) Int. Cl.

| | | |
|---|---|---|
| *A61B 17/29* | (2006.01) | |
| *A61B 17/32* | (2006.01) | |
| *A61B 18/14* | (2006.01) | |
| *B25J 9/16* | (2006.01) | |
| *B25J 13/02* | (2006.01) | |
| *A61B 17/00* | (2006.01) | |
| *A61B 17/068* | (2006.01) | |

(52) U.S. Cl.
CPC ... *A61B 2017/00482* (2013.01); *Y10S 901/08* (2013.01); *Y10S 901/09* (2013.01); *Y10S 901/30* (2013.01); *Y10T 29/49826* (2015.01); *Y10T 74/18056* (2015.01)

(56) References Cited

U.S. PATENT DOCUMENTS

| | | |
|---|---|---|
| 4,672,281 A | 6/1987 | Yagusic et al. |
| 4,830,569 A | 5/1989 | Jannborg |
| 4,872,803 A | 10/1989 | Asakawa |
| 5,214,969 A | 6/1993 | Adkins et al. |
| 5,603,723 A | 2/1997 | Aranyi et al. |
| 5,632,432 A | 5/1997 | Schulze et al. |
| 5,649,956 A | 7/1997 | Jensen et al. |
| 5,656,903 A | 8/1997 | Shui et al. |
| 5,712,543 A | 1/1998 | Sjostrom |
| 5,760,530 A | 6/1998 | Kolesar |
| 5,762,458 A | 6/1998 | Wang et al. |
| 5,784,542 A | 7/1998 | Ohm et al. |
| 5,817,119 A | 10/1998 | Klieman et al. |
| 5,836,869 A | 11/1998 | Kudo et al. |
| 5,855,583 A | 1/1999 | Wang et al. |
| 5,871,493 A | 2/1999 | Sjostrom et al. |
| 5,876,325 A | 3/1999 | Mizuno et al. |
| 6,007,550 A | 12/1999 | Wang et al. |
| 6,063,095 A | 5/2000 | Wang et al. |
| 6,082,797 A | 7/2000 | Antonette |
| 6,090,122 A | 7/2000 | Sjostrom et al. |
| 6,102,850 A | 8/2000 | Wang et al. |
| 6,132,368 A | 10/2000 | Cooper |
| 6,132,441 A | 10/2000 | Grace |
| 6,206,903 B1 | 3/2001 | Ramans |
| 6,246,200 B1 | 6/2001 | Blumenkranz et al. |
| 6,328,752 B1 | 12/2001 | Sjostrom et al. |
| 6,346,072 B1 | 2/2002 | Cooper |
| 6,430,473 B1 | 8/2002 | Lee et al. |
| 6,436,107 B1 | 8/2002 | Wang et al. |
| 6,441,577 B2 | 8/2002 | Blumenkranz et al. |
| 6,557,558 B1 | 5/2003 | Tajima et al. |
| 6,574,355 B2 | 6/2003 | Green |
| 6,587,750 B2 | 7/2003 | Gerbi et al. |
| 6,602,185 B1 | 8/2003 | Uchikubo |
| 6,645,196 B1 | 11/2003 | Nixon et al. |
| 6,666,876 B2 | 12/2003 | Kawai et al. |
| 6,676,684 B1 | 1/2004 | Morley et al. |
| 6,685,698 B2 | 2/2004 | Morley et al. |
| 6,699,177 B1 | 3/2004 | Laby et al. |
| 6,746,443 B1 | 6/2004 | Morley et al. |
| 6,783,524 B2 | 8/2004 | Anderson et al. |
| 6,786,896 B1 | 9/2004 | Madhani et al. |
| 6,853,879 B2 | 2/2005 | Sunaoshi |
| 6,866,671 B2 | 3/2005 | Tierney et al. |
| 6,905,460 B2 | 6/2005 | Wang et al. |
| 6,913,613 B2 | 7/2005 | Schwarz et al. |
| 7,083,571 B2 | 8/2006 | Wang et al. |
| 7,101,363 B2 | 9/2006 | Nishizawa et al. |
| 7,107,124 B2 | 9/2006 | Green |
| 7,118,582 B1 | 10/2006 | Wang et al. |
| 7,273,488 B2 | 9/2007 | Nakamura et al. |
| 7,295,893 B2 | 11/2007 | Sunaoshi |
| 7,313,464 B1 | 12/2007 | Perreault et al. |
| 7,331,967 B2 | 2/2008 | Lee et al. |
| 7,357,774 B2 | 4/2008 | Cooper |
| 7,373,219 B2 | 5/2008 | Nowlin et al. |
| 7,422,592 B2 | 9/2008 | Morley et al. |
| 7,476,237 B2 | 1/2009 | Taniguchi et al. |
| 7,549,998 B2 | 6/2009 | Braun |
| 7,594,912 B2 | 9/2009 | Cooper et al. |
| 7,608,083 B2 | 10/2009 | Lee et al. |
| 7,654,431 B2 | 2/2010 | Hueil et al. |
| 7,666,191 B2 | 2/2010 | Orban, III et al. |
| 7,674,255 B2 | 3/2010 | Braun |
| 7,695,481 B2 | 4/2010 | Wang et al. |
| 7,699,835 B2 | 4/2010 | Lee et al. |
| 7,699,855 B2 | 4/2010 | Anderson et al. |
| 7,778,733 B2 | 8/2010 | Nowlin et al. |
| 7,819,884 B2 | 10/2010 | Lee et al. |
| 7,819,885 B2 | 10/2010 | Cooper |
| 7,862,579 B2 | 1/2011 | Ortiz et al. |
| 7,865,266 B2 | 1/2011 | Moll et al. |
| 7,955,321 B2 | 6/2011 | Kishi et al. |
| 8,105,320 B2 | 1/2012 | Manzo |
| 8,155,479 B2 | 4/2012 | Hoffman et al. |
| 8,267,958 B2 | 9/2012 | Braun |
| 8,350,806 B2 | 1/2013 | Nagasaka et al. |
| 8,423,118 B2 | 4/2013 | Wenzel et al. |
| 8,423,186 B2 | 4/2013 | Itkowitz et al. |
| 8,460,277 B2 | 6/2013 | Suarez et al. |
| 8,496,647 B2 | 7/2013 | Blumenkranz et al. |
| 8,540,748 B2 | 9/2013 | Murphy et al. |
| 8,744,137 B2 | 6/2014 | Sakai et al. |
| 8,845,681 B2 | 9/2014 | Grace |
| 8,876,858 B2 | 11/2014 | Braun |
| 8,888,789 B2 | 11/2014 | Prisco et al. |
| 8,903,549 B2 | 12/2014 | Itkowitz et al. |
| 8,906,002 B2 | 12/2014 | Kishi et al. |
| 9,039,681 B2 | 5/2015 | Wang et al. |
| 9,283,675 B2 | 3/2016 | Hager et al. |
| 9,308,009 B2 * | 4/2016 | Madan ............ A61B 17/00234 |
| 9,308,646 B2 | 4/2016 | Lim et al. |
| 2001/0021859 A1 | 9/2001 | Kawai et al. |
| 2001/0055062 A1 | 12/2001 | Shioda et al. |
| 2002/0072736 A1 | 6/2002 | Tierney et al. |
| 2002/0091374 A1 | 7/2002 | Cooper |
| 2002/0128552 A1 | 9/2002 | Nowlin et al. |
| 2003/0033204 A1 | 2/2003 | Watanabe |
| 2003/0060927 A1 | 3/2003 | Gerbi et al. |
| 2003/0069471 A1 | 4/2003 | Nakanishi et al. |
| 2003/0083648 A1 | 5/2003 | Wang et al. |
| 2003/0100817 A1 | 5/2003 | Wang et al. |
| 2003/0216723 A1 | 11/2003 | Shinmura et al. |
| 2004/0049205 A1 | 3/2004 | Lee et al. |
| 2004/0092912 A1 | 5/2004 | Jinno et al. |
| 2004/0111113 A1 | 6/2004 | Nakamura et al. |
| 2004/0140787 A1 | 7/2004 | Okamoto et al. |
| 2004/0186345 A1 | 9/2004 | Yang et al. |
| 2004/0186624 A1 | 9/2004 | Oda et al. |
| 2004/0243147 A1 | 12/2004 | Lipow |
| 2004/0246469 A1 | 12/2004 | Hirose |
| 2005/0020876 A1 | 1/2005 | Shioda et al. |
| 2005/0021050 A1 | 1/2005 | Cooper |
| 2005/0033117 A1 | 2/2005 | Ozaki et al. |
| 2005/0125027 A1 | 6/2005 | Knodel et al. |
| 2005/0149003 A1 | 7/2005 | Tierney et al. |
| 2005/0228365 A1 | 10/2005 | Wang et al. |
| 2005/0273086 A1 | 12/2005 | Green et al. |
| 2006/0052664 A1 | 3/2006 | Julian et al. |
| 2006/0074408 A1 | 4/2006 | Jinno et al. |
| 2006/0079865 A1 | 4/2006 | Jinno et al. |
| 2006/0079866 A1 | 4/2006 | Jinno et al. |
| 2006/0087746 A1 | 4/2006 | Lipow |
| 2006/0116973 A1 | 6/2006 | Okamoto et al. |
| 2006/0149162 A1 | 7/2006 | Daw et al. |
| 2006/0155262 A1 | 7/2006 | Kishi et al. |
| 2006/0161138 A1 | 7/2006 | Orban, III et al. |
| 2006/0190031 A1 | 8/2006 | Wales et al. |
| 2006/0235436 A1 | 10/2006 | Anderson et al. |
| 2007/0012135 A1 | 1/2007 | Tierney et al. |
| 2007/0089557 A1 | 4/2007 | Solomon et al. |

(56) References Cited

U.S. PATENT DOCUMENTS

| | | |
|---|---|---|
| 2007/0119274 A1 | 5/2007 | Devengenzo et al. |
| 2007/0137372 A1 | 6/2007 | Devengenzo et al. |
| 2007/0138992 A1 | 6/2007 | Prisco et al. |
| 2007/0142823 A1 | 6/2007 | Prisco et al. |
| 2007/0142825 A1 | 6/2007 | Prisco et al. |
| 2007/0156122 A1 | 7/2007 | Cooper |
| 2007/0167679 A1 | 7/2007 | Miyamoto et al. |
| 2007/0167680 A1 | 7/2007 | Miyamoto et al. |
| 2007/0173689 A1 | 7/2007 | Ozaki et al. |
| 2007/0197896 A1 | 8/2007 | Moll et al. |
| 2007/0208375 A1 | 9/2007 | Nishizawa et al. |
| 2007/0219668 A1 | 9/2007 | Takahashi et al. |
| 2007/0225550 A1 | 9/2007 | Gattani et al. |
| 2007/0249897 A1 | 10/2007 | Miyamoto et al. |
| 2007/0265638 A1 | 11/2007 | Lipow et al. |
| 2008/0015611 A1 | 1/2008 | Jinno et al. |
| 2008/0033240 A1 | 2/2008 | Hoffman et al. |
| 2008/0046122 A1 | 2/2008 | Manzo et al. |
| 2008/0051631 A1 | 2/2008 | Dejima et al. |
| 2008/0059131 A1 | 3/2008 | Tokita et al. |
| 2008/0103524 A1 | 5/2008 | Grace |
| 2008/0140088 A1 | 6/2008 | Orban, III |
| 2008/0147091 A1 | 6/2008 | Cooper |
| 2008/0177285 A1 | 7/2008 | Brock et al. |
| 2008/0204425 A1 | 8/2008 | Nagasaka et al. |
| 2008/0215065 A1 | 9/2008 | Wang et al. |
| 2008/0228196 A1 | 9/2008 | Wang et al. |
| 2008/0234866 A1 | 9/2008 | Kishi et al. |
| 2008/0243142 A1 | 10/2008 | Gildenberg |
| 2008/0262654 A1 | 10/2008 | Omori et al. |
| 2008/0287735 A1 | 11/2008 | Takemoto et al. |
| 2008/0312668 A1 | 12/2008 | Grace |
| 2009/0018700 A1 | 1/2009 | Okamoto et al. |
| 2009/0022262 A1 | 1/2009 | Ohishi |
| 2009/0030273 A1 | 1/2009 | Murakami |
| 2009/0034820 A1 | 2/2009 | Sugiyama |
| 2009/0036736 A1 | 2/2009 | Dejima et al. |
| 2009/0036902 A1 | 2/2009 | DiMaio et al. |
| 2009/0046146 A1 | 2/2009 | Hoyt |
| 2009/0057369 A1 | 3/2009 | Smith et al. |
| 2009/0088634 A1 | 4/2009 | Zhao et al. |
| 2009/0088773 A1 | 4/2009 | Zhao et al. |
| 2009/0088897 A1 | 4/2009 | Zhao et al. |
| 2009/0132088 A1 | 5/2009 | Taitler |
| 2009/0163948 A1 | 6/2009 | Sunaoshi et al. |
| 2009/0171147 A1 | 7/2009 | Lee et al. |
| 2009/0182193 A1 | 7/2009 | Whitman et al. |
| 2009/0193299 A1 | 7/2009 | Sekiguchi et al. |
| 2009/0204911 A1 | 8/2009 | Sekiguchi et al. |
| 2009/0247877 A1 | 10/2009 | Tanaka et al. |
| 2009/0281378 A1 | 11/2009 | Banju et al. |
| 2009/0326318 A1 | 12/2009 | Tognaccini et al. |
| 2010/0010673 A1 | 1/2010 | Wang et al. |
| 2010/0013812 A1 | 1/2010 | Gu et al. |
| 2010/0087835 A1 | 4/2010 | Blumenkranz et al. |
| 2010/0160728 A1 | 6/2010 | Yoshie |
| 2010/0163057 A1 | 7/2010 | Anderson et al. |
| 2010/0174293 A1 | 7/2010 | Orban, III et al. |
| 2010/0217284 A1 | 8/2010 | Grace |
| 2010/0217528 A1 | 8/2010 | Sato et al. |
| 2010/0225209 A1 | 9/2010 | Goldberg et al. |
| 2010/0228264 A1 | 9/2010 | Robinson et al. |
| 2010/0228265 A1 | 9/2010 | Prisco |
| 2010/0234857 A1 | 9/2010 | Itkowitz et al. |
| 2010/0274087 A1 | 10/2010 | Diolaiti et al. |
| 2010/0291520 A1 | 11/2010 | Kurenov et al. |
| 2010/0317965 A1 | 12/2010 | Itkowitz et al. |
| 2010/0318099 A1 | 12/2010 | Itkowitz et al. |
| 2010/0318101 A1 | 12/2010 | Choi |
| 2010/0332031 A1 | 12/2010 | Itkowitz et al. |
| 2011/0015650 A1 | 1/2011 | Choi et al. |
| 2011/0050852 A1 | 3/2011 | Lamprecht et al. |
| 2011/0118707 A1 | 5/2011 | Burbank |
| 2011/0118748 A1 | 5/2011 | Itkowitz |
| 2011/0118753 A1 | 5/2011 | Itkowitz et al. |
| 2011/0137337 A1 | 6/2011 | van den Dool et al. |
| 2011/0190932 A1 | 8/2011 | Tsusaka et al. |
| 2011/0230894 A1 | 9/2011 | Simaan et al. |
| 2011/0238079 A1 | 9/2011 | Hannaford et al. |
| 2011/0276058 A1 | 11/2011 | Choi et al. |
| 2011/0279374 A1 | 11/2011 | Park et al. |
| 2011/0282493 A1 | 11/2011 | Ortmaier |
| 2011/0288579 A1 | 11/2011 | Hyodo |
| 2011/0306952 A1 | 12/2011 | Chen et al. |
| 2012/0071752 A1 | 3/2012 | Sewell et al. |
| 2012/0165828 A1 | 6/2012 | Duque et al. |
| 2012/0191245 A1 | 7/2012 | Fudaba et al. |

FOREIGN PATENT DOCUMENTS

| | | |
|---|---|---|
| CN | 101426412 A | 5/2009 |
| DE | 10 2008 041 867 A1 | 3/2010 |
| EP | 0 677 278 A1 | 10/1995 |
| EP | 1 728 475 A2 | 12/2006 |
| EP | 2 092 875 A1 | 8/2009 |
| EP | 2 298 220 A1 | 3/2011 |
| EP | 2 332 484 A2 | 6/2011 |
| JP | 63-029810 A | 2/1988 |
| JP | 64-034688 A | 2/1989 |
| JP | 01-271185 A | 10/1989 |
| JP | 02-071980 A | 3/1990 |
| JP | 02-292193 A | 12/1990 |
| JP | 03-161289 A | 7/1991 |
| JP | 05-096477 A | 4/1993 |
| JP | 5-329784 A | 12/1993 |
| JP | 07-001366 A | 1/1995 |
| JP | 07-194609 A | 8/1995 |
| JP | 07-241300 A | 9/1995 |
| JP | 07-246578 A | 9/1995 |
| JP | 07-096182 B2 | 10/1995 |
| JP | 8-66883 A | 3/1996 |
| JP | 08-215204 A | 8/1996 |
| JP | 08-243080 A | 9/1996 |
| JP | H10-502265 A | 3/1998 |
| JP | 10-128538 A | 5/1998 |
| JP | 11-300662 A | 11/1999 |
| JP | 2000-312684 A | 11/2000 |
| JP | 2001-087281 A | 4/2001 |
| JP | 2001-113481 A | 4/2001 |
| JP | 2001-277157 A | 10/2001 |
| JP | 2001-309920 A | 11/2001 |
| JP | 2002-014287 A | 1/2002 |
| JP | 2002-059380 A | 2/2002 |
| JP | 2002-102248 A | 4/2002 |
| JP | 2002-272758 A | 9/2002 |
| JP | 2002-537884 A | 11/2002 |
| JP | 2003-024336 A | 1/2003 |
| JP | 2003-053685 A | 2/2003 |
| JP | 2003-250812 A | 9/2003 |
| JP | 2003-265500 A | 9/2003 |
| JP | 2003-340752 A | 12/2003 |
| JP | 2004-105451 A | 4/2004 |
| JP | 2004-114201 A | 4/2004 |
| JP | 2005-511185 A | 4/2005 |
| JP | 2005-192743 A | 7/2005 |
| JP | 3686947 B2 | 8/2005 |
| JP | 2005-261827 A | 9/2005 |
| JP | 2005-283600 A | 10/2005 |
| JP | 2005-312991 A | 11/2005 |
| JP | 2006-061272 A | 3/2006 |
| JP | 2006-167867 A | 6/2006 |
| JP | 2006-288955 A | 10/2006 |
| JP | 2006-321027 A | 11/2006 |
| JP | 2007-029274 A | 2/2007 |
| JP | 2007-038315 A | 2/2007 |
| JP | 2007-98507 A | 4/2007 |
| JP | 2007-105485 A | 4/2007 |
| JP | 3999816 B2 | 10/2007 |
| JP | 2008-000282 A | 1/2008 |
| JP | 2008-036793 A | 2/2008 |
| JP | 4058113 B2 | 3/2008 |
| JP | 2008-093270 A | 4/2008 |
| JP | 2008-104854 A | 5/2008 |
| JP | 2008-514357 A | 5/2008 |

(56) References Cited

FOREIGN PATENT DOCUMENTS

| | | |
|---|---|---|
| JP | 2008-173724 A | 7/2008 |
| JP | 4129313 B | 8/2008 |
| JP | 4176126 B2 | 11/2008 |
| JP | 2009-028157 A | 2/2009 |
| JP | 2009-056164 A | 3/2009 |
| JP | 2009-512514 A | 3/2009 |
| JP | 2009-520573 A | 5/2009 |
| JP | 2009-178230 A | 8/2009 |
| JP | 2009-178541 A | 8/2009 |
| JP | 2009-530037 A | 8/2009 |
| JP | 2009-195694 A | 9/2009 |
| JP | 2009-226029 A | 10/2009 |
| JP | 2009-226093 A | 10/2009 |
| JP | 2009-269127 A | 11/2009 |
| JP | 2010-504127 A | 2/2010 |
| JP | 2010-076012 A | 4/2010 |
| JP | 2010-524548 A | 7/2010 |
| JP | 2011-509112 A | 3/2011 |
| JP | 2011-206213 A | 10/2011 |
| JP | 2012-000199 A | 1/2012 |
| JP | 2012-012104 A | 1/2012 |
| JP | 2012-091310 A | 5/2012 |
| WO | 96/00044 A1 | 1/1996 |
| WO | 97/16123 A1 | 5/1997 |
| WO | 97/16124 A1 | 5/1997 |
| WO | 97/29690 A1 | 8/1997 |
| WO | 98/25666 A1 | 6/1998 |
| WO | WO 00/51486 A1 | 9/2000 |
| WO | 00/60421 A2 | 10/2000 |
| WO | WO 03/049596 A2 | 6/2003 |
| WO | 2006/039092 A2 | 4/2006 |
| WO | 2006/111966 A2 | 10/2006 |
| WO | WO 2007/047782 A2 | 4/2007 |
| WO | WO 2007/075864 A1 | 7/2007 |
| WO | WO 2007/111955 A2 | 10/2007 |
| WO | WO 2007/126443 A2 | 11/2007 |
| WO | WO 2007/138674 A1 | 12/2007 |
| WO | WO 2008/038184 A2 | 4/2008 |
| WO | WO 2008/108289 A1 | 9/2008 |
| WO | WO 2009034477 A2 | 3/2009 |
| WO | 2009/089614 A1 | 7/2009 |
| WO | WO 2010006057 A1 | 1/2010 |
| WO | 2010/093152 A2 | 8/2010 |
| WO | WO 2010109932 A1 | 9/2010 |
| WO | 2010/126127 A1 | 11/2010 |
| WO | 2011/025786 A1 | 3/2011 |
| WO | 2011/060139 A2 | 5/2011 |
| WO | 2011/060185 A1 | 5/2011 |
| WO | 2011/060187 A1 | 5/2011 |
| WO | 2011/085815 A1 | 7/2011 |
| WO | WO 2012/042949 A1 | 4/2012 |

OTHER PUBLICATIONS

International Search Report dated Sep. 4, 2012 issued in PCT/JP2012/070408.
International Search Report dated Aug. 28, 2012 issued in PCT/JP2012/069927.
International Search Report dated Sep. 4, 2012 issued in PCT/JP2012/070415.
International Search Report dated Oct. 16, 2012 issued in PCT/JP2012/070581.
International Search Report dated Nov. 13, 2012 issued in PCT/JP2012/070576.
International Search Report dated Sep. 18, 2012 issued in PCT/JP2012/070417.
International Search Report dated Oct. 30, 2012 issued in PCT/JP2012/070418.
International Search Report dated Sep. 11, 2012 issued in PCT/JP2012/070416.
International Search Report dated Sep. 18, 2012 issued in PCT/JP2012/070407.
International Search Report dated Sep. 18, 2012 issued in PCT/JP2012/069868.
International Search Report dated Nov. 6, 2012 issued in PCT/JP2012/069919.
International Search Report dated Sep. 11, 2012 issued in PCT/JP2012/069696.
U.S. Office Action dated Apr. 9, 2015 received in related U.S. Patent Application, namely U.S. Appl. No. 14/169,675.
U.S. Office Action dated May 8, 2015 received in related U.S. Patent Application, namely U.S. Appl. No. 14/157,920.
Chinese Office Action dated Jun. 3, 2015 from related Chinese Application No. 201280035926.3, together with an English language translation.
Chinese Office Action dated Jul. 1, 2015 from related Chinese Application No. 201280037244.6, together with an English language translation.
Extended Supplementary European Search Report dated Jul. 1, 2015 from related European Application No. 12 82 0066.4.
Extended Supplementary European Search Report dated Jul. 2, 2015 from related European Application No. 12 81 9672.2.
Extended Supplementary European Search Report dated Jul. 23, 2015 from related European Application No. 12 81 9455.2.
Notice of Allowance dated Jan. 20, 2015 from related U.S. Appl. No. 13/566,023.
Notice of Allowance dated Jan. 29, 2015 from related U.S. Appl. No. 14/168,551.
Extended Supplementary European Search Report dated Feb. 12, 2015 from related European Application No. 12 81 9447.9.
Extended Supplementary European Search Report dated Feb. 13, 2015 from related European Application No. 12 82 0679.4.
Supplementary European Search Report dated Feb. 18, 2015 from related European Application No. 12 82 0758.6.
Extended Supplementary European Search Report dated Feb. 23, 2015 from related European Application No. 12 81 9877.7.
Extended Supplementary European Search Report dated Feb. 23, 2015 from related European Application No. 12 82 0239.7.
Partial Supplementary European Search Report dated Feb. 26, 2015 from related European Application No. 12 82 0066.4.
Partial Supplementary European Search Report dated Feb. 27, 2015 from related European Application No. 12 81 9672.2.
Extended Supplementary European Search Report dated Mar. 2, 2015 from related European Application No. 12 82 0017.7.
Extended Supplementary European Search Report dated Mar. 16, 2015 from related European Application No. 12 82 0479.9.
Extended Supplementary European Search Report dated Mar. 16, 2015 from related European Application No. 12 81 9504.7.
Extended Supplementary European Search Report dated Mar. 16, 2015 from related European Application No. 12 81 9398.4.
Office Action dated Mar. 25, 2015 received in related U.S. Patent Application, namely U.S. Appl. No. 14/169,321.
Extended Supplementary European Search Report dated Mar. 27, 2015 from related European Application No. 12 82 0056.5.
Office Action dated Sep. 16, 2015 received in related U.S. Patent Application, namely U.S. Appl. No. 13/566,012.
Office Action dated Oct. 19, 2015 received in related U.S. Patent Application, namely U.S. Appl. No. 14/168,525.
Office Action dated Oct. 22, 2015 received in related U.S. Patent Application, namely U.S. Appl. No. 14/151,987.
Office Action dated Nov. 19, 2015 received in related U.S. Patent Application, namely U.S. Appl. No. 14/157,920.
Japanese Office Action dated Jan. 19, 2016 from related Japanese Patent Application No. 2012-036226, together with an English language translation.
Office Action dated Feb. 22, 2016 received in related U.S Appl. No. 14/168,496.
Office Action dated Mar. 10, 2016 received in related U.S Appl. No. 13/566,012.
Office Action dated Mar. 24, 2016 received in related U.S. Appl. No. 13/566,047.
English Abstract of JP 01-234140 dated Sep. 19, 1989.
English Abstract of WO 0051486 A1 dated Sep. 8, 2000.
European Patent Office Communication dated May 23, 2016 in related European Application No. 12 819 877.7.

(56) References Cited

OTHER PUBLICATIONS

Japanese Office Action dated Jun. 14, 2016 in related Japanese Patent Application No. 2012-012104.
Office Action dated Jun. 16, 2016 received in related U.S. Appl. No. 14/169,742.
Japanese Office Action dated Jun. 28, 2016 in related Japanese Patent Application No. 2013-526973.
Japanese Office Action dated Apr. 26, 2016 from related Japanese Patent Application No. 2012-157788.
Japanese Office Action dated Apr. 26, 2016 from related Japanese Patent Application No. 2012-154945.
Notice of Allowance dated Apr. 22, 2016 issued in U.S. Appl. No. 14/157,920.

* cited by examiner

MEDICAL EQUIPMENT

This application is a continuation application based on PCT Patent Application No. PCT/JP2012/070407, filed Aug. 3, 2012, claiming priority based on Provisional Application No. 61/515,203 filed in U.S. on Aug. 4, 2011, and Japanese Patent Application No. 2012-154945 filed on Jul. 10, 2012, the contents of which are incorporated herein by reference.

BACKGROUND OF THE INVENTION

Field of the Invention

The invention relates to medical equipment, and more specifically, to medical equipment providing high work efficiency when a surgical instrument is replaced.

Description of the Related Art

In the past, as an operation support system, a medical manipulator system having a master manipulator manipulated by an operator and a slave manipulator giving medical treatment based on operation of the master manipulator is known.

For example, a medical robot system having a master manipulator, a slave manipulator, and a display screen displaying, for instance, an image of a medical treatment target is disclosed in Published Japanese Translation No. 2009-512514 of the PCT International Publication.

The medical robot system disclosed in Published Japanese Translation No. 2009-512514 of the PCT International Publication has two master input devices operated by a hand of an operator, and slave arms connected to the master input devices in pairs. Thus, the slave arms operated in response to operation of the master input devices can be switched using a switch.

Further, in medical equipment, a device capable of separating a manipulating part grasped by an operator and a surgical instrument performing medical treatment on a medical treatment target is known. For example, a manipulator having a surgical instrument (working part) that can be detached from a manipulation instructing part is disclosed in Japanese Unexamined Patent Application, First Publication No. 2009-226093.

SUMMARY OF THE INVENTION

According to a first aspect of the invention, a medical equipment includes: a surgical instrument having a movable part to perform medical treatment on a target spot; an actuator configured to operate the movable part; and a detachable interface installed on the surgical instrument and configured to attachably and detachably couple the surgical instrument to the actuator. The detachable interface includes an origin return mechanism configured to move the movable part to a predetermined origin position when the surgical instrument is detached from the actuator.

According to a second aspect of the invention, in the medical equipment according to the first aspect, the origin return mechanism may include: a moving member connected to the movable part to be contactable with the actuator, having an initial position when spaced apart from the actuator, and moved from the initial position by contact with the actuator; and a return member configured to move the displacing member to the initial position.

According to a third aspect of the invention, in the medical equipment according to the second aspect, the return member may include a biasing member configured to bias the moving member and to cause the moving member to be moved to the initial position.

According to a fourth aspect of the invention, in the medical equipment according to the third aspect, the medical equipment may include a regulating member configured to regulate movement of the moving member by the biasing member.

According to a fifth aspect of the invention, in the medical equipment according to the fourth aspect, the regulating member may include an adjustment part configured to adjust an amount of the movement of the moving member.

According to a sixth aspect of the invention, in the medical equipment according to any one of the third to fifth aspects, the biasing member may include a damper.

According to a seventh aspect of the invention, in the medical equipment according to any one of the two to sixth aspects, the actuator may include: a shaft body configured to be rotated; and a power source configured to rotate the shaft body using a central axis of the shaft body as a rotational center. The moving member may be a rotary member engaged with the shaft body and rotated along with the shaft body. The rotary member may be coupled with a first portion of a power transmission member being fixed to the movable part at a second portion of the power transmission member.

According to an eighth aspect of the invention, in the medical equipment according to the seventh aspect, the rotary member may include a cam configured to extend in a circumferential direction thereof. The return member may include a pressing member having a cam pin coming into contact with the cam and configured to press the rotary member.

According to a ninth aspect of the invention, in the medical equipment according to the eighth aspect, the rotary member may include a stopper configured to regulate a rotation of the rotary member so that the rotary member is stopped at the initial position.

According to a tenth aspect of the invention, in the medical equipment according to the seventh aspect, the rotary member may include a cam configured to extend in a circumferential direction of the rotary member, and a stopper configured to regulate a rotation of the rotary member so that the rotary member is stopped at the initial position.

According to an eleventh aspect of the invention, in the medical equipment according to the seventh aspect, the rotary member may include a string member put on an outer circumference of the rotary member; and springs fixed to the string member. The rotary member may be connected to the springs via the string member so as to go back to the initial position when no external force is applied to the springs.

According to a twelfth aspect of the invention, in the medical equipment according to any one of the first to eleventh aspects, the movable part includes an end effector configured to perform the medical treatment on the target spot.

According to a thirteenth aspect of the invention, in the medical equipment according to any one of the first to twelfth aspects, the medical equipment may include: an information recording part installed on the detachable interface and including information for specifying a type of the surgical instrument; a recognizing part configured to recognize the information recorded on the information recording part; and a control device configured to specify the surgical instrument attached to the actuator based on the information recognized by the recognizing part and to operate the surgical instrument.

According to a fourteenth aspect of the invention, in the medical equipment according to the thirteenth aspect, the information recording part may be a wireless tag configured to perform near field wireless communication, and the recognizing part may include a wireless device configured to read the information from the wireless tag.

According to a fifteenth aspect of the invention, in the medical equipment according to the thirteenth aspect, the information recording part may include a convexo-concave portion having a shape specific to the surgical instrument, and the recognizing part may include a plurality of switches in which conduction states are switched by the convexo-concave portion.

DETAILED DESCRIPTION OF THE INVENTION

Figure 1:
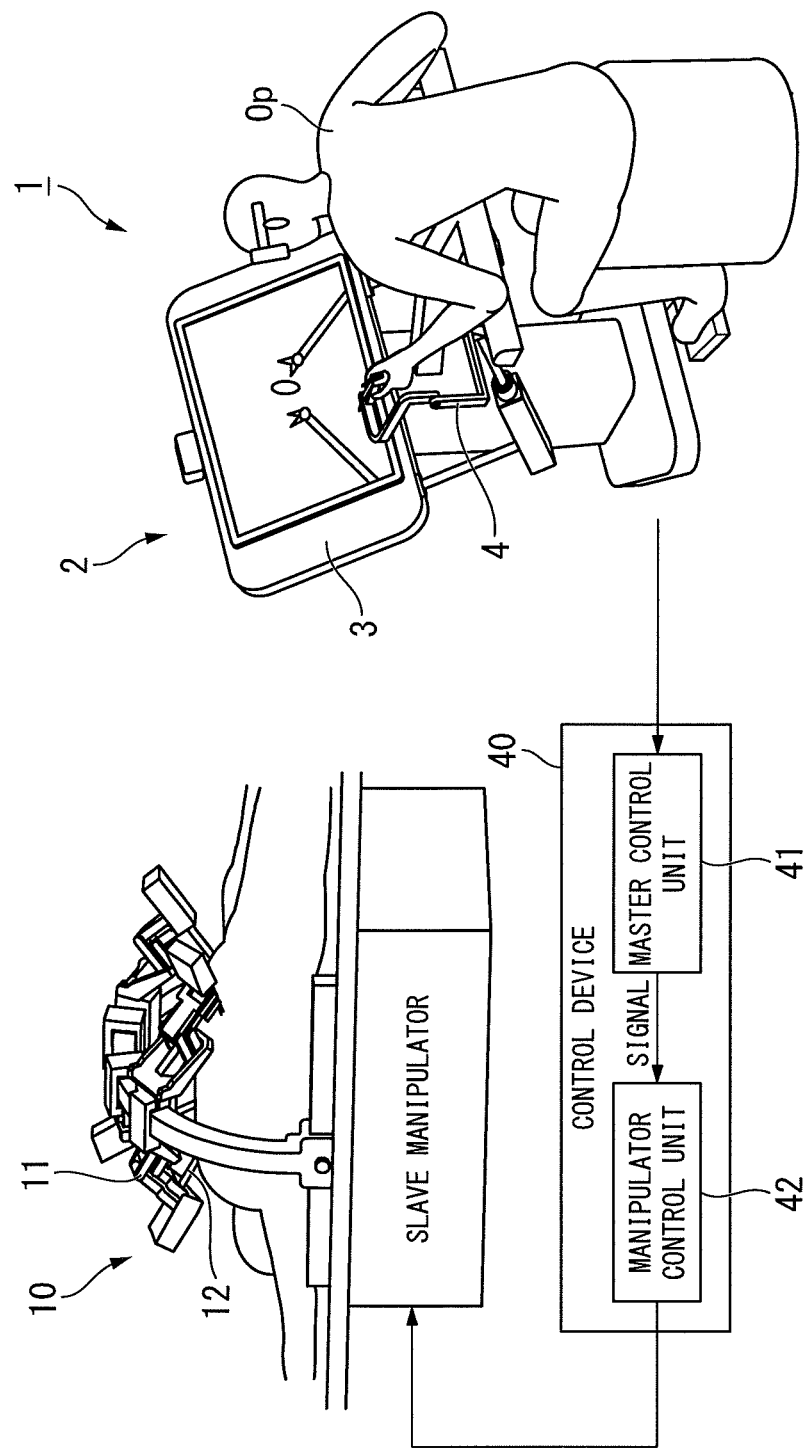
FIG. 1 is an overall view showing medical equipment according to an embodiment of the invention.

Medical equipment according to an embodiment of the invention will be described. FIG. 1 is an overall view showing medical equipment according to the embodiment. As shown in FIG. 1, the medical equipment 1 according to the present embodiment is equipment used for medical purposes as an operation support system of a master/slave mode. The medical equipment 1 includes a master manipulator 2, a slave manipulator 10, and a control device 40.

The master manipulator 2 is a device functioning as a master that transmits movement of manipulation of an operator Op to the slave manipulator 10. The master manipulator 2 includes a master display part 3 and a manipulating part 4.

The master display part 3 is a device that displays images of a surgical spot and its surroundings of a patient P which are photographed by a camera (not shown). As the master display part 3, known display devices such as liquid crystal displays or organic electroluminescence (EL) displays may be appropriately selected and employed.

The manipulating part 4 is a mechanism for transmitting the movement of the manipulation of the operator Op to the slave manipulator 10, and is connected to be able to communicate with the control device 40. Further, the manipulating part 4 is disposed in front of the master display part 3 so as to enable the operator Op to manipulate the manipulating part 4 while watching the master display part 3. When the manipulating part 4 is manipulated by the operator Op, the manipulating part 4 analyzes the movement of the manipulation and outputs a signal for driving the slave manipulator 10 to the control device 40.

Figure 2:
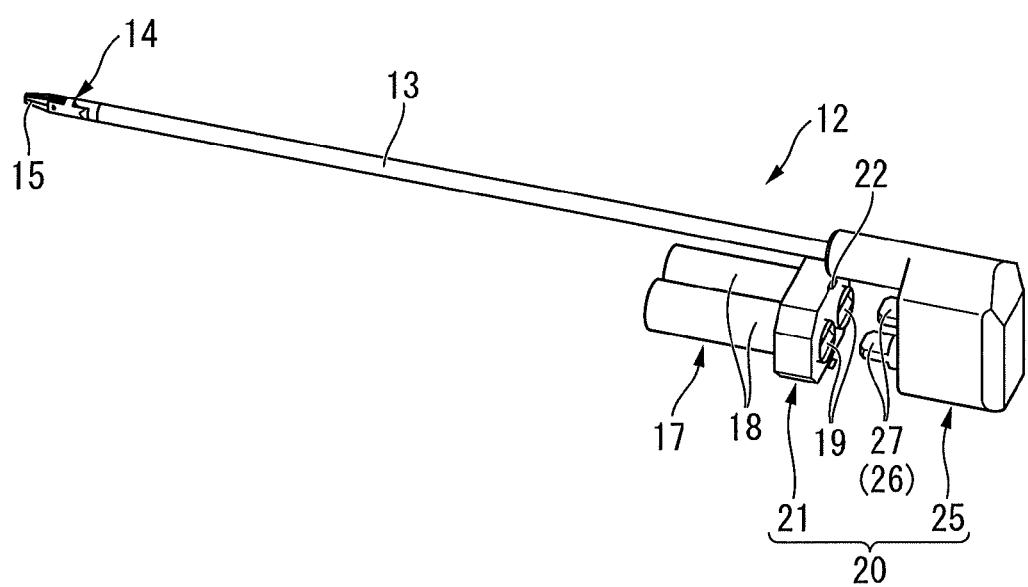
FIG. 2 is a perspective view showing a configuration of a part of a slave manipulator in the medical equipment according to the embodiment of the invention.
Figure 3:
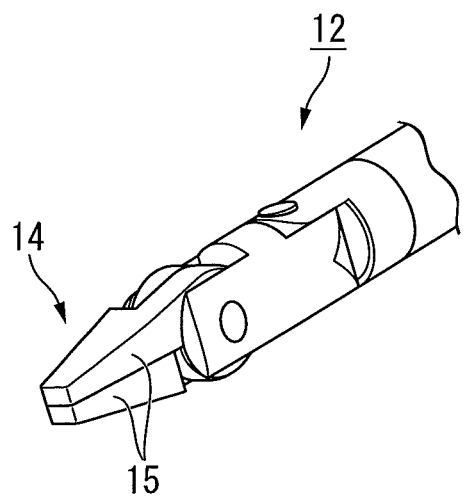
FIG. 3 is a perspective view showing a configuration of a part of a surgical instrument installed on the slave manipulator according to the embodiment of the invention.
Figure 4:
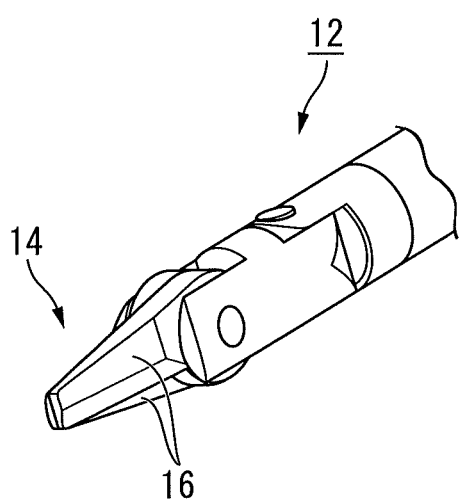
FIG. 4 is a perspective view showing another configuration of the part of the surgical instrument installed on the slave manipulator according to the embodiment of the invention.

FIG. 2 is a perspective view showing a configuration of a part of the slave manipulator 10. FIG. 3 is a perspective view showing a configuration of a part of a surgical instrument 12 installed on the slave manipulator 10. FIG. 4 is a perspective view showing another configuration of the part of the surgical instrument 12 installed on the slave manipulator 10.

As shown in FIGS. 1 and 2, the slave manipulator 10 includes a slave arm 11, a surgical instrument 12, an actuator 17, and a detachable interface 20.

The slave arm 11 is an arm having a joint with single degree of freedom or more. The slave arm 11 is operated in response to the operation of the master manipulator 2 by power supplied from a power source (not shown). In the present embodiment, a plurality of slave arms 11 are installed on the slave manipulator 10.

The surgical instrument 12 includes an insertion part 13 inserted into a human body, an end effector (movable part) 14 installed on the insertion part 13, and a wire (power transmission member) W (see FIG. 5) for transmitting an operation force magnitude to the end effector 14.

The insertion part 13 is a rigid or flexible cylindrical member, and has the wire W inserted thereinto. The end effector 14 is attached to one end of the insertion part 13, and a distal side interface 25 that is a part of the detachable interface 20 is attached to the other end of the insertion part 13.

As the end effector 14, instruments used in medical practices such as surgery may be appropriately selected and employed. For example, as the end effector 14, as shown in FIGS. 3 and 4, a forceps 15 or scissors 16 may be used. In the following description, the grasping forceps 15 on which a pair of openable/closable forceps pieces are installed may be given as an example of the end effector 14. The end effector 14 has an origin position decided when the medical equipment 1 begins to be used. The origin position in the end effector 14 is a position that is considered not to damage living body tissue that is a target spot. For example, the grasping forceps 15, which is the end effector 14 in the present embodiment, is configured so that its completely opened state is set to the origin position. Thereby, when the end effector 14 returns to the origin position in use, the end effector 14 can be prevented from being grasped the living body tissue unintentionally. The origin position is not limited to the completely opened state, and thus may be set to a completely closed state, or a state between the completely opened state and the completely closed state.

As shown in FIG. 2, the actuator 17 is installed to drive the wire W via the detachable interface 20. The actuator 17 includes servo motors 18 serving as power sources, and shaft bodies 19 rotated by the servo motors 18.

Figure 5:
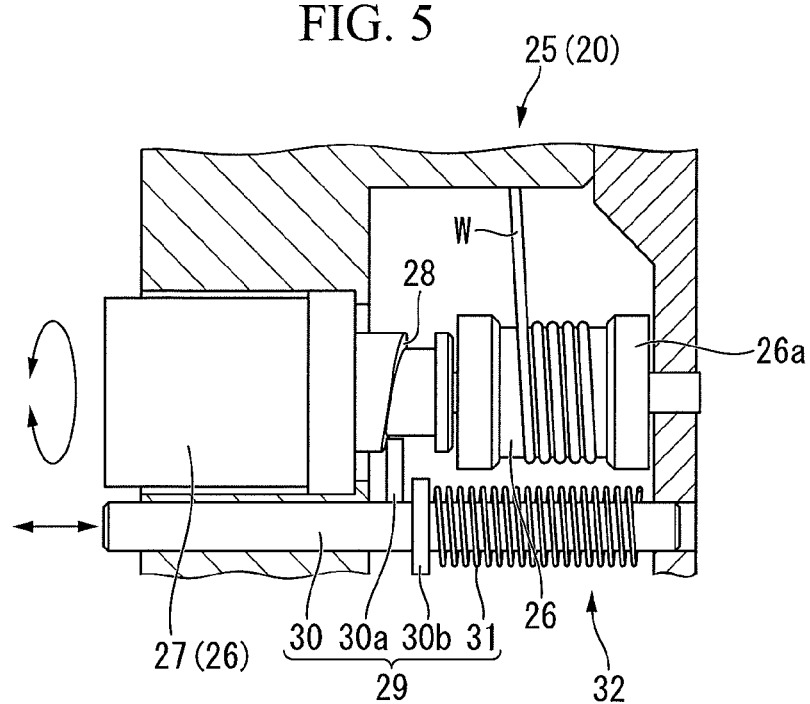
FIG. 5 is a partial cross-sectional view showing a configuration of a part of a detachable interface in the slave manipulator according to the embodiment of the invention.
Figure 6:
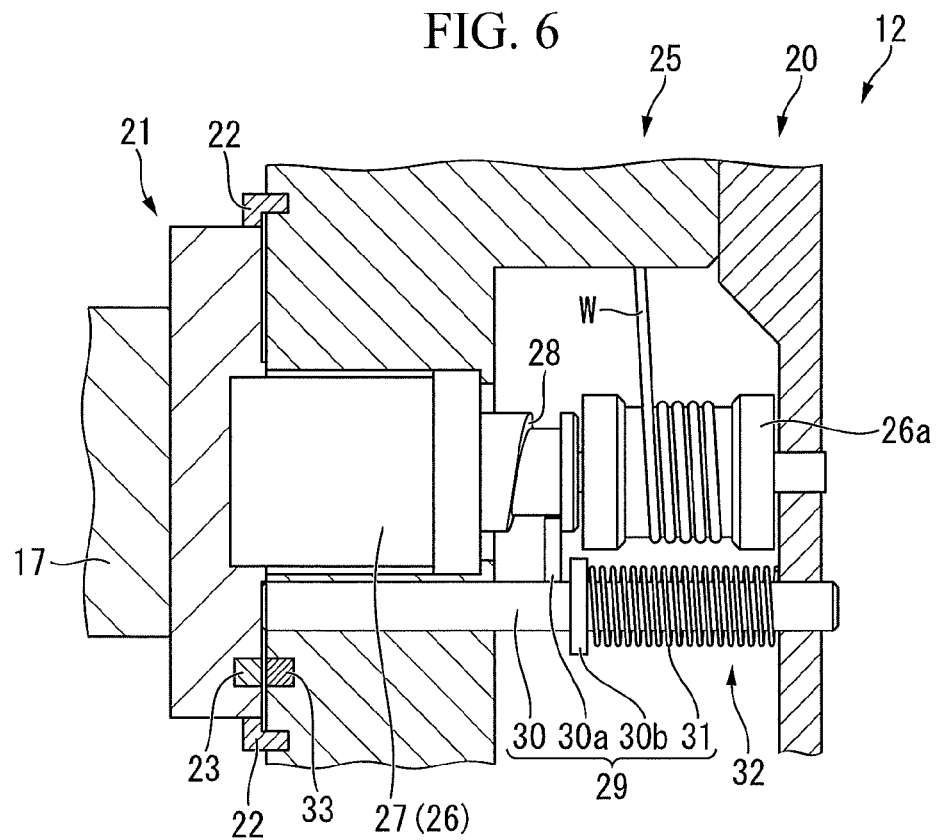
FIG. 6 is a partial cross-sectional view showing a configuration of a part of a detachable interface in the slave manipulator according to the embodiment of the invention.
Figure 7:
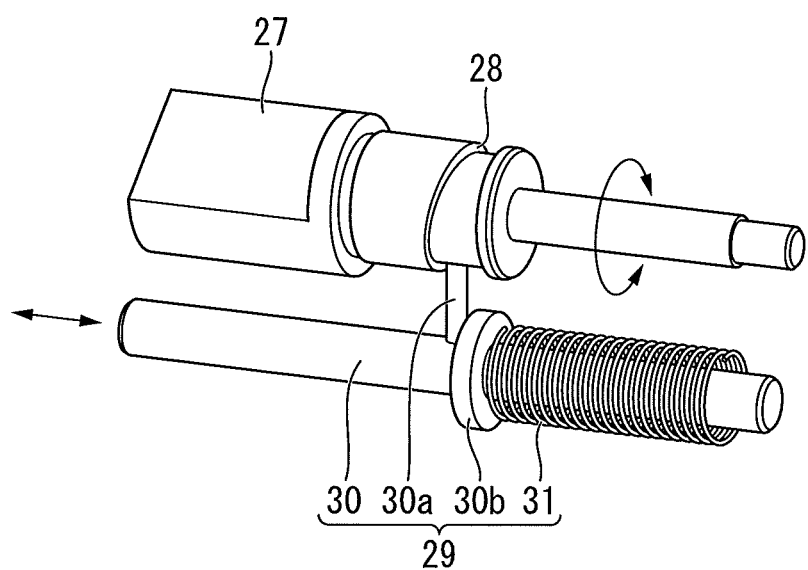
FIG. 7 is a perspective view showing a configuration of a part of a distal side interface in the slave manipulator according to the embodiment of the invention.

FIG. 5 is a partial cross-sectional view showing a configuration of a part of the detachable interface 20 in the slave manipulator 10. FIG. 6 is a partial cross-sectional view showing the configuration of the part of the detachable interface 20 in the slave manipulator 10. FIG. 7 is a perspective view showing a configuration of a part of the distal side interface 25 in the slave manipulator 10.

The detachable interface 20 includes a proximal side interface 21 attached to the slave arm 11 and the distal side interface 25 attached to the surgical instrument 12.

As shown in FIGS. 2 and 6, the proximal side interface 21 is fixed to the slave arm 11, and is coupled to the actuator 17. A lock mechanism 22 and a sensor (recognition part) 23 are attached to the proximal side interface 21. The lock mechanism 22 is engaged with the distal side interface 25. The sensor 23 is used for discriminating a type of the surgical instrument 12.

The lock mechanism 22 is installed to manually fix the distal side interface 25 to the proximal side interface 21.

The sensor 23 is a device that reads information stored in a wireless tag 33 to be described below. The sensor 23 can discriminate the type of the surgical instrument 12 based on the information stored in the wireless tag 33. Thereby, the sensor 23 enables the actuator 17 to perform an operation corresponding to the type of the surgical instrument 12 attached to the proximal side interface 21.

The distal side interface 25 includes a moving member 26, a return member 29, and a wireless tag (information recording part) 33. The moving member 26 is attachably and detachably installed on each shaft body 19 of the actuator 17. The return member 29 is a member for returning the moving member 26 to a predetermined origin position. The wireless tag 33 has information for specifying the type of the surgical instrument 12. In the present embodiment, the wireless tag 33 is a tag specialized in near field wireless communication having restricted communicable coverage to be able to communicate with the sensor 23 within a very short distance. That is, the wireless tag 33 is configured to prevent interference with a communication of another surgical instrument 12 brought into a surgery room.

The moving member 26 is provided with a roller 26a, and the wire W for operating the end effector 14 is coupled to the roller 26a. Further, the moving member 26 is a rotary member 27 that can contact each shaft body 19 of the actuator 17. The rotary member 27 is rotated around a rotational axis of the shaft body 19 by power from the servo motor 18. When the rotary member 27 is rotated, a part of the wire W is wound on or unwound from an outer circumferential surface of the roller 26a. Thereby, the end effector 14 is operated by the wire W.

As shown in FIGS. 6 and 7, the rotary member 27 is provided with an inclined cam 28 formed in a partial helical shape adopting a rotational center of the rotary member 27 as a central line.

The return member 29 includes a pressing member 30 coming into contact with the inclined cam 28, and a biasing member 31 biasing the pressing member 30.

The pressing member 30 includes a cam pin 30a for pressing the inclined cam 28 so that the rotary member 27 is rotated around a rotational center toward an initial position. The pressing member 30 is a rod-like member that is pressed by the biasing member 31 and thereby protrudes from the distal side interface 25. The pressing member 30 is configured to attach the distal side interface 25 to the proximal side interface 21 and thereby to be forcibly pushed into the distal side interface 25. That is, the pressing member 30 moves advanced or retreat in contact with the proximal side interface 21. In the state in which the pressing member 30 is forcibly pushed into the distal side interface 25 by the proximal side interface 21, the pressing member 30 is kept away from the inclined cam 28.

The biasing member 31 is a member that biases the pressing member 30 in the rotational center direction of the rotary member 27. In the present embodiment, the biasing member 31 is made up of a compression spring, and is located at an outer circumferential side of the pressing member 30. One end of the compression spring constituting the biasing member 31 is in contact with a flange part 30b of the pressing member 30, whereas the other end of the compression spring constituting the biasing member 31 is in contact with a housing of the distal side interface 25. The biasing member 31 is expanded or compressed in parallel with the rotational center direction of the rotary member 27, and moves the pressing member 30 in parallel with the rotational center direction of the rotary member 27. Specifically, when the rotary member 27 rotates from the initial position toward the maximum rotational position, the biasing member 31 is compressed via the pressing member 30. When the rotary member 27 rotates from the maximum rotational position toward the initial position, the compression of the biasing member 31 is released by the pressing member 30. When the rotary member 27 is located at the initial position, the biasing member 31 slightly compresses the pressing member 30. When the rotary member 27 is not coupled with the actuator 17, the biasing member 31 is biased so that it is difficult for the rotary member 27 to deviate from the initial position toward the maximum rotational position.

In the present embodiment, the initial position and maximum rotational position of the rotary member 27 are determined by the inclined cam 28 and the pressing member 30 corresponding to the origin position and the movable range in the end effector 14. Specifically, the position of the rotary member 27 is the initial position when the pressing member 30 is pressed to the extreme by a biasing force of the biasing member 31. Further, the maximum rotational position is a rotational angle from the initial position, and the rotational angle is regulated by the control device 40 controlling the actuator 17.

In the present embodiment, an origin return mechanism 32 that returns the end effector 14 to the origin position is made up of the moving member 26 and the return member 29.

As shown in FIG. 1, the control device 40 includes a master control unit 41 and a manipulator control unit 42.

The master control unit 41 receives a signal output from the master manipulator 2, and generates a signal for operating the slave manipulator 10. Furthermore, the master control unit 41 outputs the signal generated in the master control unit 41 to the manipulator control unit 42.

The manipulator control unit 42 generates a signal for operating the slave manipulator 10 based on the signal received from the master control unit 41, and outputs the generated signal to the slave manipulator 10. In the present embodiment, the manipulator control unit 42 operates at least the slave arm 11 and the actuator 17 according to the signal from the master control unit 41.

Figure 8:
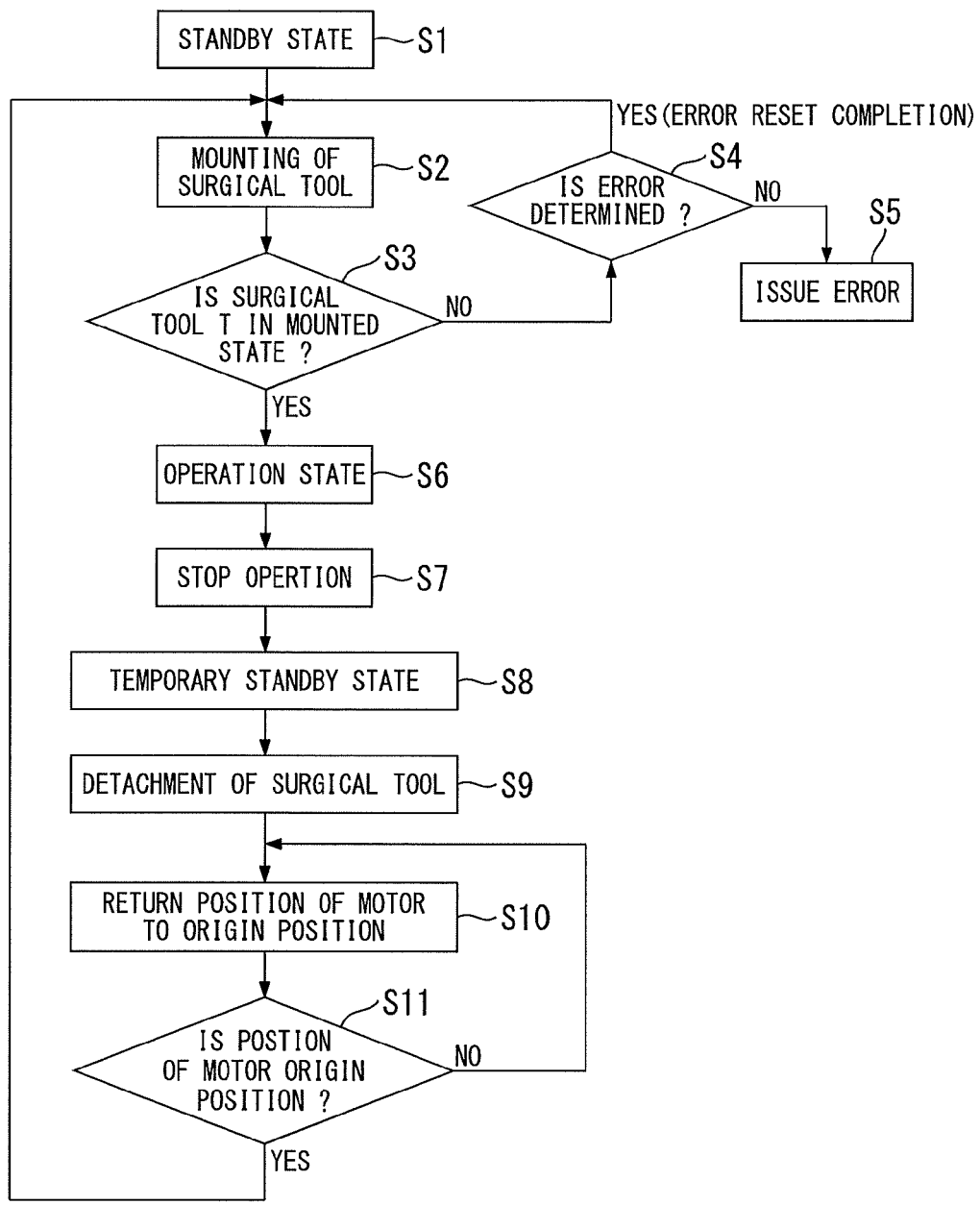
FIG. 8 is a flowchart for describing an operation of the medical equipment when used in accordance with the embodiment of the invention.

Next, an operation of the medical equipment 1 will be described. FIG. 8 is a flowchart for describing an operation of the medical equipment 1 when used.

In the present embodiment, the medical equipment 1 has a plurality of surgical instruments 12. Each surgical instrument 12 is capable of being attached to the proximal side interface 21, and has the similar distal side interface 25. The distal side interfaces 25 installed on the respective surgical instruments 12 are provided with the wireless tags 33 having different identifiers.

First, the medical equipment 1 is started up, and enters a standby state (step S1 shown in FIG. 8).

When the medical equipment 1 according to the present embodiment is used in surgery, the entirety thereof is favorably sterilized or each surgical instrument 12 disposed at a distal side farther than the distal side interface 25 is favorably sterilized. In this case, the proximal side interfaces 21 and the surgical instruments 12 can be favorably sterilized. The components (e.g., slave arms 11) of the proximal side nearer than the proximal side interfaces 21 may be covered with sterilized drapes.

Subsequently, if necessary, the surgical instruments 12 are attached to the slave arms 11 by manual work of an operator Op or another method (step S2).

Specifically, in step S2, the distal side interface 25 is fixed to the proximal side interface 21, and thus the surgical instrument 12 is attached to the slave arm 11. Thereby, the rotary member 27 disposed at the distal side interface 25 is engaged with the shaft body 19 disposed at the proximal side interface 21. The rotary member 27 is engaged with the shaft body 19, and thus can be rotated along with the shaft body 19.

Furthermore, since the wireless tag 33 and the sensor 23 are in an adjacent state, the sensor 23 can read information from the wireless tag 33. The control device 40 makes reference to the information of the wireless tag 33 via the sensor 23, and determines whether or not the surgical instrument 12 is in a mounted state (step S3).

If the information from the wireless tag 33 is not read, it is determined that the surgical instrument 12 is not in the mounted state, and thus an error determination (step S4) is made. For example, in step S3, a message such as "surgical instrument demounted" is displayed on the master display part 3, and a message inquiring about the necessity to mount the surgical instrument 12 is sent. In step S3, for example, when the surgical instrument 12 is not correctly attached to the slave arm 11 due to an error in the mounting method of the surgical instrument 12, the surgical instrument 12 is reset. Thereby, the error is recovered, and the process proceeds to step S6 through steps S2 and S3.

If the slave arm 11 on which the surgical instrument 12 is not mounted is present, an error code indicating that the surgical instrument 12 is not mounted is sent (step S5). In the present embodiment, with regard to each of the slave arms 11 to which the surgical instrument 12 can be attached, it is determined whether or not the surgical instrument 12 is attached to the slave arm 11. Thereby, the slave arm 11 to which the surgical instrument 12 is attached and the slave arm 11 to which the surgical instrument 12 is not attached can be distinguished. Further, if necessary, using the error code obtained in step S5, the slave arm 11 to which the surgical instrument 12 is not attached may be evacuated to a position out of the way or be set to a non-use state in which no response is made to the signal from the master manipulator 2.

If the surgical instrument 12 is correctly attached without an error in attaching the surgical instrument 12, it is determined that the surgical instrument 12 is mounted on the slave arm 11, and the process proceeds to step S6.

Step S6 is a step of keeping the medical equipment 1 operable, and using the surgical instrument 12 to perform medical treatment.

When the surgical instrument 12 is used, the surgical instrument 12 attached to the actuator 17 can be specified based on the information of the wireless tag 33 recognized by the sensor 23, and an operation corresponding to a type of the surgical instrument 12 can be performed. The surgical instrument 12 is operated by the manipulating part 4 installed on the master manipulator 2.

Thereby, step S6 is terminated. When the surgical instrument 12 attached to the slave arm 11 does not need to be replaced, the overall manipulation may be terminated with the processes before step S6.

When the surgical instrument 12 attached to the slave arm 11 is replaced, the process proceeds to step S6.

Step S7 is a step of temporarily stopping an operation in order to replace the surgical instrument 12.

In step S7, when there occurs a need to detach the surgical instrument 12 from the slave arm 11 of the medical equipment 1, the operator Op of the medical equipment 1 stops the operation of the surgical instrument 12, and evacuates the surgical instrument 12 to a safe position. The movement of the surgical instrument 12 is performed using the manipulating part 4 of the master manipulator 2. For example, the grasping forceps 15 is separated from a target spot, thereby moving the surgical instrument 12 to the safe position.

The operation of evacuating the surgical instrument 12 to the safe position may be automatically performed by the slave manipulator 10. In this case, a position of living body tissue may be detected, and means for deciding a movement path of the surgical instrument 12 so that the surgical instrument 12 does not come into contact with the living body tissue may be installed on the slave manipulator 10. The surgical instrument 12 may be evacuated by the corresponding means. Thereby, step S7 is terminated, and the process proceeds to step S8.

Step S8 is a step of changing the medical equipment 1 in a standby state. In this step, a signal from the manipulating part 4 of the master manipulator 2 is cancelled, and thus the slave manipulator 10 is not operated. For this reason, the operator Op can come into contact with the slave manipulator 10. After step S8, the medical equipment 1 is kept on standby until it is changed in an operable state.

Step S9 is a step of detaching the surgical instrument 12 in the medical equipment 1 that is in the standby state.

In step S9, to detach the distal side interface 25 from the proximal side interface 21, the lock mechanism 22 is released. Furthermore, the proximal side interface 21 is separated from the distal side interface 25 so that the shaft bodies 19 and the rotary members 27 are disengaged from each other.

Since the signal for operating the servo motors 18 is cancelled in step S8, the shaft bodies 19 are easily separated from the rotary members 27 so that no torque is applied from the shaft bodies 19 toward the rotary members 27. When the shaft bodies 19 are separated from the rotary members 27, the rotary members 27 can be freely rotated. Furthermore, the state that the pressing member 30 is pressed by the proximal side interface 21 is also released by separation of the distal side interface 25 from the proximal side interface 21.

The pressing member 30 is coupled to the rotary member 27 via the inclined cam 28. The pressing member 30 presses the inclined cam 28 in a direction in which the rotary member 27 is moved to the initial position by the biasing force of the biasing member 31. The pressing member 30 presses the inclined cam 28 of the rotary member 27, and thereby the rotary member 27 is rotated from the maximum rotational position toward the initial position. When the rotary member 27 is rotated from the maximum rotational position toward the initial position, the wire W wound on the outer circumferential surface of the rotary member 27 causes a pair of pieces of the forceps 15 to be moved to the origin position.

Thereby, when the distal side interface 25 is detached from the proximal side interface 21, the grasping forceps 15 is powered by the biasing force of the biasing member 31 to return to the origin position regardless of the opened/closed state of the grasping forceps 15 prior to the detachment. That is, when the surgical instrument 12 is detached from the slave arm 11, the end effector 14 of the surgical instrument 12 returns to the origin position. Thereby, step S9 is terminated, and the process proceeds to step S10.

Step S10 is a step of operating the actuator 17 to return the shaft bodies 19 to the position of the initial state.

In step S10, the shaft bodies 19 are moved and stopped so as to correspond to the initial position of the rotary members 27 by the actuator 17 attached to the proximal side interface 21.

The actuator 17 in the present embodiment has the servo motors 18, and position information thereof is fed back by a servo mechanism. Thereby, it is determined whether or not the shaft bodies 19 correctly return to the initial state by means of the actuator 17 (step S11), and the shaft bodies 19 return to the initial state with high precision.

After step S11 is terminated, another surgical instrument 12a that is a replace target of the surgical instrument 12 can be attached to the slave arm 11 as needed.

Since the other surgical instrument 12a has the distal side interface 25 in the present embodiment, the end effector 14 is located at the origin position. In the proximal side interface 21, the shaft bodies 19 are reset to the initial state. Thereby, the alignment between the shaft bodies 19 and the rotary members 27 is previously completed, and the distal side interface 25 can be easily attached to the proximal side interface 21.

Furthermore, it is discriminated by wireless communication between the wireless tag 33 and the sensor 23 that the other surgical instrument 12a is attached, and the master manipulator 2 can send a new signal according to an operational sequence corresponding to the other surgical instrument 12a.

Even when the other surgical instrument 12a is mounted, the surgical instrument 12a is allowed to be used after being determined that the surgical instrument 12a is correctly attached based on a series of processes from step S2 to step S6 described above.

As described above, in the present embodiment, the origin return mechanism 32 moves the end effector 14 to a predetermined origin position when the surgical instrument 12 is detached from the actuator 17. Thereby, when the other surgical instrument 12a is attached after the surgical instrument 12 is detached, no alignment is required. Further, even when the detached surgical instrument 12 is attached again, the end effector 14 is always located at the origin position, and thus no position confirmation is required. Thereby, in the medical equipment 1 according to the present embodiment, the work efficiency is high when the surgical instrument 12 is replaced.

Further, since the biasing member 31 is installed on the return member 29, the end effector 14 can automatically return to the origin position in response to the detaching operation of the distal side interface 25.

The sensor 23 recognizes the information stored in the wireless tag 33, and thereby the type of the surgical instrument 12 can be distinguished. For this reason, for example, when the surgical instrument 12, which differs in the type of the end effector 14, is replaced and used, it is possible to automatically input information about the end effector 14 to the master manipulator 2. Further, since the type of the surgical instrument 12 can be transmitted by the wireless communication, a metal terminal for transmitting the type of the surgical instrument 12 is not required, and even in an environment in which there is a high possibility of wetting due to clean, cleanliness is kept without corrosion and favorable communication can be provided.

First Modified Example

Figure 9:
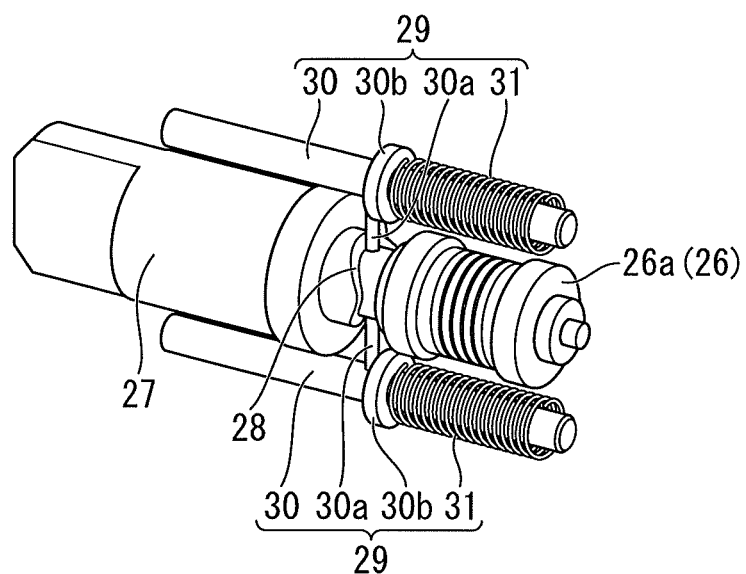
FIG. 9 is a perspective view showing a configuration of the medical equipment of a first modified example of the embodiment of the invention.

Next, a modified example of the aforementioned embodiment will be described. FIG. 9 is a perspective view showing a configuration of a first modified example of the medical equipment according to the present embodiment.

As shown in FIG. 9, in the present modified example, the pressing member 30 and the biasing member 31 are further provided in a set, and the structure of the inclined cam 28 is different. That is, in the present modified example, two pressing members 30 are disposed so as to face each other in a radial direction of the rotary member 27, and the biasing members 31 are installed on the respective pressing members 30.

This configuration also produces an effect similar to that of the aforementioned embodiment. Further, since the inclined cam 28 can be pressed at opposite positions by the two pressing members 30, the rotary member 27 is rotated smoothly.

Figure 10:
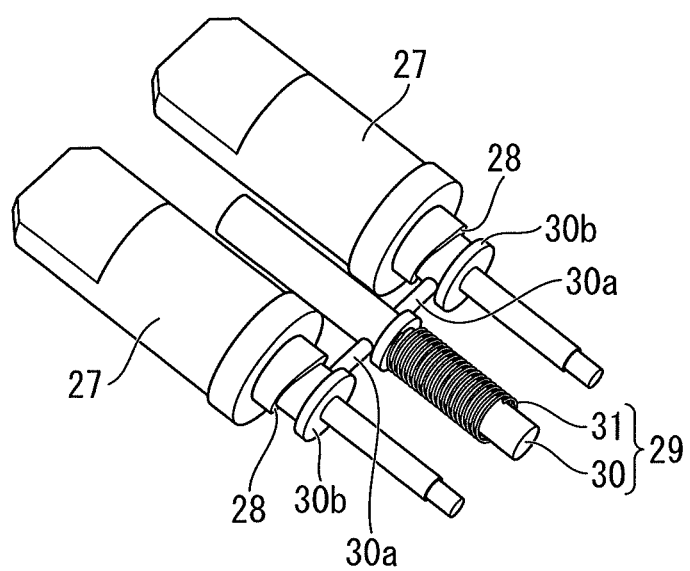
FIG. 10 is a perspective view showing another configuration in the first modified example.

Further, FIG. 10 is a perspective view showing another configuration in the present modified example. As shown in FIG. 10, in contrast to the present modified example, a plurality of rotary members 27 may be rotated by a set of the pressing member 30 and the biasing member 31. For example, in the end effector 14 having two or more degrees of freedom, the rotary members 27 are provided by the number corresponding to the degrees of freedom, and thus these rotary members 27 can return to the initial position by the set of the pressing member 30 and the biasing member 31.

Second Modified Example

Figure 11:
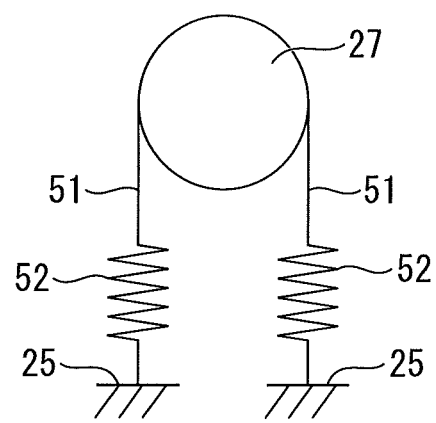
FIG. 11 is a schematic diagram showing the medical equipment of a second modified example of the embodiment of the invention.

Next, a second modified example of the aforementioned embodiment will be described. FIG. 11 is a schematic diagram showing a configuration of the present modified example.

As shown in FIG. 11, in the present modified example, in place of the pressing member 30, a string member 51 put on an outer circumference of the rotary member 27 and springs 52 fixed to the string member 51 are provided.

In the present modified example, one ends of tension springs as the springs 52 are fixed to both ends of the string member 51, respectively. Another ends of the tension springs are fixed to a part of the housing of the distal side interface 25. The tension springs fixed to the string member are equal load springs.

This configuration also produces an effect similar to that of the aforementioned embodiment. Further, in the present modified example, the rotary member 27 can be smoothly rotated as frictional resistance is smaller than in the aforementioned embodiment which using the cam.

Third Modified Example

Figure 12:
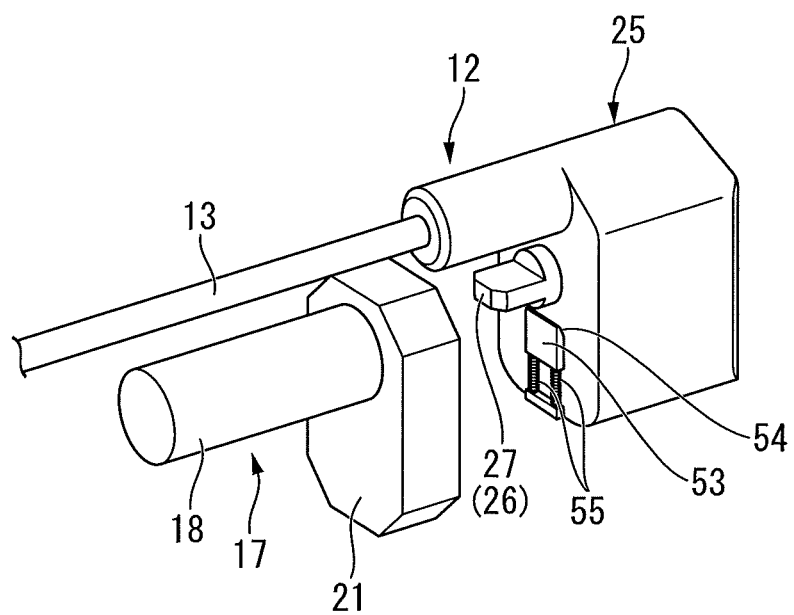
FIG. 12 is a perspective view showing the medical equipment of a third modified example of the embodiment of the invention.
Figure 13:
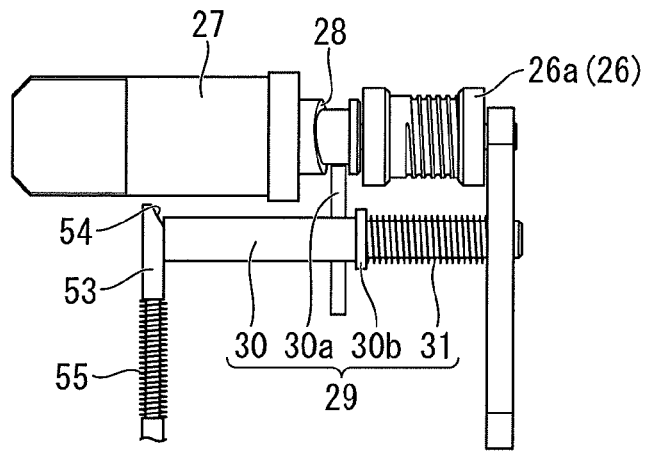
FIG. 13 is a side view showing a configuration of the medical equipment of the third modified example of the embodiment of the invention.
Figure 14:
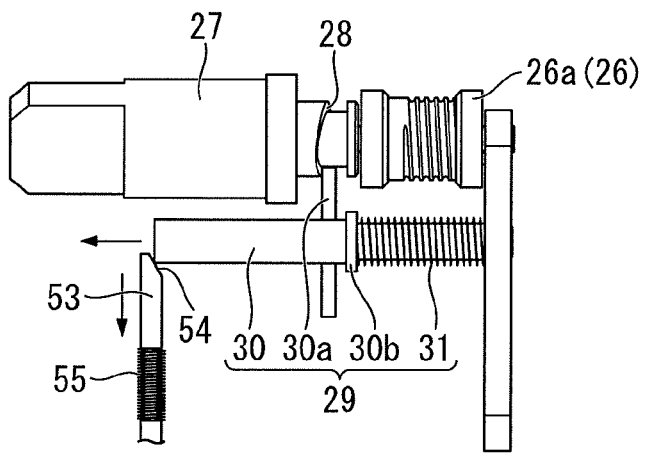
FIG. 14 is a view for describing an operation when used in the third modified example.
Figure 15:
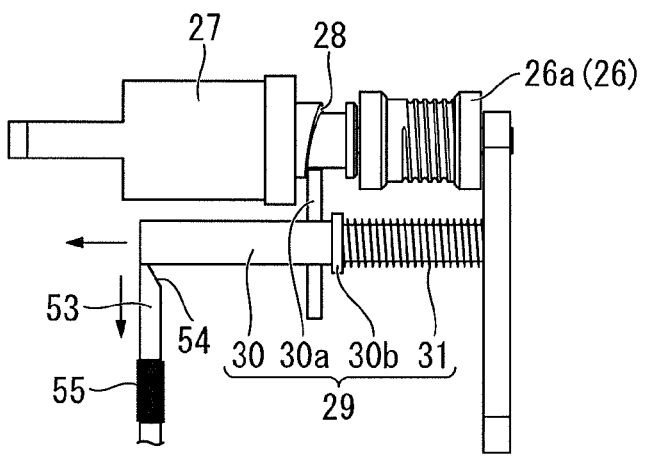
FIG. 15 is a view for describing an operation when used in the third modified example.

Next, a third modified example of the aforementioned embodiment will be described. FIG. 12 is a perspective view showing a configuration of the present modified example. FIG. 13 is a side view showing a configuration of the present modified example. FIGS. 14 and 15 are views for describing an operation when used in the present modified example.

As shown FIGS. 12 and 13, in the present modified example, there is a difference in that a regulating member 53 regulating movement of the rotary member 27 (moving member 26) using the biasing member 31 is provided.

The regulating member 53 is a plate-shaped member that enters a part of a movement path of the pressing member 30 to be able to regulate forward/backward movement of the pressing member 30 in a rotational center direction of the rotary member 27.

Further, as shown in FIG. 13, the regulating member 53 is provided with a tapered part (adjustment part) 54. The tapered part 54 functions as a slope that gradually moves the pressing member 30 according to an amount to which the regulating member 53 is pulled out from the inside of the movement path of the pressing member 30. Furthermore, the regulating member 53 has a spring 55. The spring 55 can press the regulating member 53 into the movement path of the pressing member 30 after the pressing member 30 passes in the movement path of the pressing member 30.

With this configuration, the pressing member 30 is not moved only by detaching the distal side interface 25 from the proximal side interface 21. After releasing the movement regulation of the pressing member 30 regulated by the regulating member 53, the pressing member 30 is moved, and thus the rotary member 27 is moved to the initial position. Thereby, for example, when the distal side interface 25 leaves the proximal side interface 21 unintentionally, unnecessary movement of the end effector 14 can be suppressed.

The tapered part 54 is formed on the regulating member 53. Thereby, as shown in FIGS. 13 to 15, the position of the pressing member 30 can be adjusted to control an amount of rotation of the rotary member 27.

Since the spring 55 is installed on the regulating member 53, the regulating member 53 is not required to be pressed into the movement path of the pressing member 30 with manual work, and thus only the operation of attaching the distal side interface 25 to the proximal side interface 21 may be performed.

The biasing member 31 described in the aforementioned embodiment may include a damper. Thereby, when the distal side interface 25 is detached from the proximal side interface 21, the end effector 14 slowly returns to the origin position.

Further, in the aforementioned embodiment, as the biasing member 31, a compression spring has been described by way of example. However, the biasing member 31 may be a rubber member. For example, the pressing member 30 may be configured to install the rubber member in place of the compression spring, and to be biased using a repulsion force of the rubber member.

Further, a stopper regulating the rotatable range of the rotary member 27 may be formed in the housing of the distal side interface 25. In this case, the initial position and the maximum rotational position of the rotary member 27 can be regulated with high precision.

Figure 16:
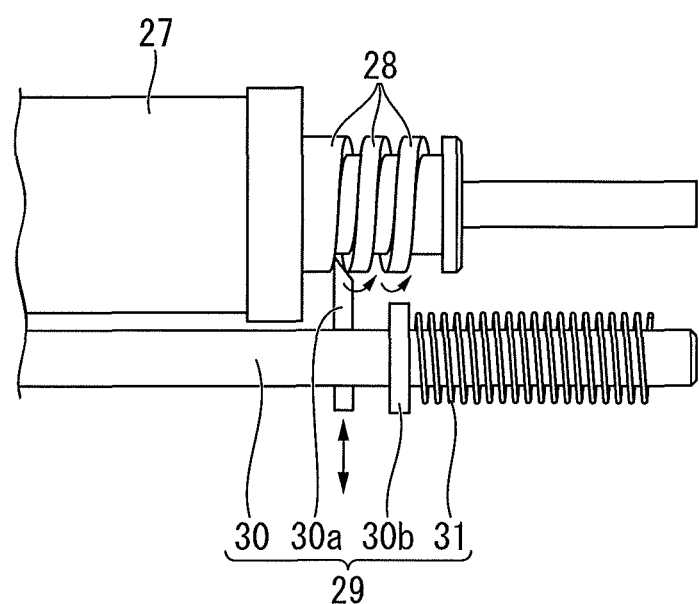
FIG. 16 is a side view showing an example of design change of the embodiment.

Also, the inclined cam 28 described in the embodiment may be a cam having two or more turns wound in a circumferential direction of the rotary member 27. FIG. 16 is a side view showing an example of design change of the aforementioned embodiment. As shown in FIG. 16, in this case, the pressing member 30 engaged with the inclined cam 28 may include a ratchet mechanism in which a cam pin 30a can move forward or backward in a radial direction of the rotary member 27. That is, in this case, when the pressing member 30 is pressed in by the proximal side interface 21, the pressing member 30 is moved by jumping across an adjacent groove in the inclined cam 28. When the pressing caused by the proximal side interface 21 is released, the pressing member 30 is moved along the grooves of the inclined cam 28.

Further, as the means for discriminating the type of the surgical instrument 12, the configuration based on the wireless tag 33 and the sensor 23 has been given as an example. However, the discriminating means is not limited to this configuration. For example, a convexo-concave portion having a unique shape corresponding to the type of the surgical instrument 12 and a switch in which a combination of conduction states is formed by this convexo-concave portion may be included.

In the present embodiment, the end effector 14 has been given as an example of the movable part. However, the movable part may include a structure such as a joint for deforming the surgical instrument 12 such as for bending the distal end of the surgical instrument 12. That is, the joint may be moved to a predetermined origin position by a configuration similar to the origin return mechanism of the aforementioned embodiment.

In addition, the components represented in the embodiment and the modified examples may be appropriately combined and configured.

The design change of the specific configuration is not limited to the above details.

While preferred embodiments of the present invention have been described and illustrated above, it should be understood that these are exemplary of the present invention and are not to be considered as limiting. Additions, omissions, substitutions, and other modifications can be made without departing from the spirit or scope of the present invention. Accordingly, the present invention is not to be considered as being limited by the foregoing description, and is only limited by the scope of the appended claims.

What is claimed is:

1. A medical equipment comprising:
    an actuator configured to generate rotary motion about a first axis; and
    a surgical instrument comprising:
        an end effector configured to move;
        a rotary member configured to be detachably connected to the actuator,
            wherein the rotary member is configured to rotate about a second axis, coaxial with the first axis, in accordance with receiving the rotary motion to move the end effector; and
        an origin return mechanism configured to rotate the rotary member about the second axis to a predetermined origin position when the rotary member is detached from the actuator.
2. The medical equipment according to claim 1,
    wherein the origin return mechanism comprises:
        a moving member connected to the rotary member, wherein the moving member is configured to be rotated by the rotary member about the second axis to move the end effector; and a return member configured to contact the moving member such that the moving member rotates the rotary member about the second axis to the predetermined origin position.

3. The medical equipment according to claim 2, wherein the return member comprises a biasing member configured to bias the moving member and to cause the moving member to rotate the rotary member about the second axis to the predetermined origin position.

4. The medical equipment according to claim 3, further comprising a regulating member configured to regulate movement of the moving member by the biasing member.

5. The medical equipment according to claim 4, wherein the regulating member comprises an adjustment part configured to adjust an amount of the movement of the moving member.

6. The medical equipment according to claim 3, wherein the biasing member comprises a damper.

7. The medical equipment according to claim 2, wherein the actuator comprises:
   a shaft body configured to be rotated; and
   a power source configured to rotate the shaft body using a central axis of the shaft body as a rotational center,
wherein the rotary member is configured to be detachably connected to the shaft body and to be rotated about the second axis along with the shaft body, and
wherein the surgical instrument further comprises a power transmission member,
   wherein a first portion of the power transmission member is coupled to the moving member, and a second portion of the power transmission member is coupled to the end effector such that the end effector is moved via the power transmission member by a rotation of the rotary member and the moving member about the second axis.

8. The medical equipment according to claim 7, wherein the moving member comprises a cam configured to extend in a circumferential direction of the moving member, and
wherein the return member comprises a cam pin configured to come into contact with and press the cam such that the moving member rotates the rotary member about the second axis to the predetermined origin position.

9. The medical equipment according to claim 8, wherein the rotary member comprises a stopper configured to regulate a rotation of the rotary member so that the rotary member is stopped at the predetermined origin position.

10. The medical equipment according to claim 7, wherein the moving member comprises a cam configured to extend in a circumferential direction of the moving member, and
wherein the rotary member comprises a stopper configured to regulate a rotation of the rotary member so that the rotary member is stopped at the predetermined origin position.

11. The medical equipment according to claim 2, wherein the return member comprises:
   a string member put on an outer circumference of the moving member; and
   springs fixed to the string member, and
wherein the moving member is connected to the springs via the string member so as to rotate the rotary member about the second axis to the predetermined origin position when no external force is applied to the springs.

12. A surgical instrument comprising:
an end effector configured to be moved;
a rotary member configured to be detachably connected to an actuator configured to generate rotary motion about a first axis, the rotary member being configured to rotate about a second axis, coaxial with the first axis, in accordance with receiving the rotary motion to move the end effector; and
an origin return mechanism configured to rotate the rotary member about the second axis to a predetermined origin position when the rotary member is detached from the actuator.

13. A medical equipment comprising:
an actuator configured to generate rotary motion; and
a surgical instrument comprising:
   an end effector configured to be moved;
   an origin return mechanism; and
   a rotary member having a connected state and a disconnected state,
      wherein in the connected state, the origin return mechanism is configured to disengage from the rotary member, and the rotary member is configured to be connected to the actuator to be rotated about a rotation axis by the rotary motion to move the end effector, and
      wherein in the disconnected state, the rotary member is configured to be disconnected from the actuator, and the origin return mechanism is configured to engage the rotary member to rotate the rotary member to a predetermined position.

14. The medical equipment according to claim 13, wherein the origin return mechanism comprises a pressing member, and
wherein in the disconnected state, the rotary member is configured to be disconnected from the actuator, and the pressing member is configured to press the rotary member to rotate the rotary member to the predetermined position.

15. A surgical instrument comprising:
an end effector configured to be moved;
an origin return mechanism; and
a rotary member having a connected state and a disconnected state,
   wherein in the connected state, the origin return mechanism is configured to disengage from the rotary member, and the rotary member is configured to be connected to an actuator configured to generate rotary motion, to be rotated about a rotation axis by the rotary motion to move the end effector, and
   wherein in the disconnected state, the rotary member is configured to be disconnected from the actuator, and the origin return mechanism is configured to engage the rotary member to rotate the rotary member to a predetermined position.

* * * * *

UNITED STATES PATENT AND TRADEMARK OFFICE
CERTIFICATE OF CORRECTION

PATENT NO. : 9,524,022 B2  Page 1 of 1
APPLICATION NO. : 14/170856
DATED : December 20, 2016
INVENTOR(S) : Shingo Nakayama It is certified that error appears in the above-identified patent and that said Letters Patent is hereby corrected as shown below:

On the Title Page

Item 30 should read:

(30) Foreign Application Priority Data

July 10, 2012   (JP).........................................2012-154945

Signed and Sealed this
Twenty-first Day of March, 2017

Michelle K. Lee
*Director of the United States Patent and Trademark Office*